United States Patent
Kim et al.

(10) Patent No.: US 9,511,026 B2
(45) Date of Patent: Dec. 6, 2016

(54) POORLY SOLUBLE DRUG CONTAINING MICROSPHERES WITH IMPROVED BIOAVAILABILITY AND METHOD OF PREPARING THE SAME

(71) Applicant: SAMYANG BIOPHARMACEUTICALS CORPORATION, Seoul (KR)

(72) Inventors: Kyung-Hee Kim, Daejeon (KR); Hyun-Ki Lee, Seoul (KR); Jun-Seok Hwang, Daejeon (KR); Su-Jong Hwang, Daejeon (KR); Chaul-Min Pai, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 14/192,026

(22) Filed: Feb. 27, 2014

(65) Prior Publication Data

US 2014/0175686 A1    Jun. 26, 2014

Related U.S. Application Data

(62) Division of application No. 13/322,549, filed as application No. PCT/KR2010/003366 on May 27, 2010, now abandoned.

(30) Foreign Application Priority Data

May 27, 2009    (KR) .................. 10-2009-0046355

(51) Int. Cl.
*A61K 9/16* (2006.01)
*A61K 31/522* (2006.01)

(52) U.S. Cl.
CPC ........... *A61K 9/1694* (2013.01); *A61K 9/1635* (2013.01); *A61K 9/1652* (2013.01); *A61K 31/522* (2013.01)

(58) Field of Classification Search
None
See application file for complete search history.

(56) References Cited

U.S. PATENT DOCUMENTS

| | | | |
|---|---|---|---|
| 4,895,726 A | 1/1990 | Curtet et al. | |
| 5,880,148 A | 3/1999 | Edgar et al. | |
| 6,074,670 A | 6/2000 | Stamm et al. | |
| 2003/0224059 A1 | 12/2003 | Lerner et al. | |
| 2009/0098200 A1* | 4/2009 | Temtsin Krayz et al. | .... 424/452 |

FOREIGN PATENT DOCUMENTS

| | | |
|---|---|---|
| CN | 1509711 | 7/2004 |
| JP | 3-1288 | 7/1991 |
| JP | 05-057102 | 3/1993 |
| JP | 09-301851 | 11/1997 |
| JP | 3028404 | 2/2000 |
| JP | 2000-281561 | 10/2000 |
| JP | 2004-534812 | 11/2004 |
| JP | 2006-008676 | 1/2006 |
| JP | 2007-501219 | 1/2007 |
| JP | 2007-131591 | 5/2007 |
| JP | 2007-308479 | 11/2007 |
| JP | 2008-100997 | 5/2008 |
| JP | 2008-518007 | 5/2008 |
| JP | 2008-133259 | 6/2008 |
| JP | 2011-515444 | 5/2011 |
| KR | 10-0767349 | 9/2007 |
| KR | 10-0818701 | 3/2008 |
| WO | 99-63968 | 12/1999 |
| WO | 00/40220 | 7/2000 |
| WO | 01-41765 | 6/2001 |
| WO | 03-000235 | 1/2003 |
| WO | 03/000235 | 1/2003 |
| WO | 2007/109605 | 9/2007 |
| WO | 2008/006714 | 1/2008 |
| WO | 2008/016260 | 2/2008 |
| WO | 2009/040818 | 4/2009 |
| WO | 2009-118356 | 10/2009 |
| WO | 2009-123169 | 10/2009 |

OTHER PUBLICATIONS

Australian Patent Office, Office Action of Australian Patent Application No. 2010253578, Jun. 21, 2012.

* cited by examiner

*Primary Examiner* — Tigabu Kassa
(74) *Attorney, Agent, or Firm* — Lex IP Meister, PLLC

(57) ABSTRACT

A poorly soluble drug containing microsphere with improved bioavailability, an oral formulation comprising the same, and a method of preparing the same are provided, wherein the poorly soluble drug containing microsphere is a solid dispersion wherein the poorly soluble drug is dispersed in the water-soluble polymer carrier in a noncrystalline form by spray drying, thus increasing bioavailability of the poorly soluble drug.

6 Claims, 5 Drawing Sheets

POORLY SOLUBLE DRUG CONTAINING MICROSPHERES WITH IMPROVED BIOAVAILABILITY AND METHOD OF PREPARING THE SAME

CROSS-REFERENCE TO RELATED APPLICATION

This application is a Divisional Application of U.S. patent application Ser. No. 13/322,549, which was filed on Dec. 12, 2011, which claims priority to International Application No. PCT/KR2010/003366 filed on May 27, 2010, which claims priority to Korean Patent Application No. 10-2009-0046355 filed in the Korean Intellectual Property Office on May 27, 2009, and the entire content of which is incorporated herein by reference.

TECHNICAL FIELD

The present invention relates to a poorly soluble drug containing microsphere, a pharmaceutical composition comprising the same, and a method of preparing the same. More specifically, to a poorly soluble drug containing microsphere with improved bioavailability of the poorly soluble drug, an oral formulation comprising the same, and a method of preparing the same.

BACKGROUND OF ART

Since most of newly developed drugs are poorly soluble, it is required to improve the solubility or absorption.

A method of increasing solubility of the existing poorly soluble drugs includes chemical modification and physical modification. The chemical modification includes salt addition, aqueous prodrug approach, and the like, and the physical modification includes modification of particle size or crystal form, formation of crystalline polymorph, formation of complex using a surfactant or cyclodextrin, drug dispersion using a dispersant, and the like. To increase solubility or absorption of drugs, drug formulation methods such as micronization, noncrystallization, solid dispersion formation, and the like have been suggested, among which solid dispersion formation has been widely examined as a means for dispersing a drug in an inactive carrier.

As the solid dispersion preparation method, several methods have been suggested, and particularly, a solvent method is a practical method. According to the solvent method, a drug and an aqueous polymer carrier are dissolved in a solvent such as an organic solvent, and the like, and the solvent is removed by distillation, or a drug is dissolved in a solvent and dispersed in a carrier, and then, the solvent is removed by distillation to prepare a solid dispersion.

As the solvent method, it is reported in Japanese Patent Publication No. 3-1288 and Japanese Patent No. 3028404 that a poorly soluble drug, nifedipine and a polymer substrate such as polyvinylpyrrolidone, hydroxymethylcellulose, methylcellulose, and the like are dissolved in an organic solvent, and the solution is spray dried to obtain a solid dispersion in a microgranule form wherein lactose, and the like is assembled with an aqueous polymer such as hydroxypropylcellulose.

A poorly soluble drug, fenofibrate has very low water solubility. Fenofibrate, (2-[4-(4-chlorobenzoyl)phenoxy]-2-methyl-propanoic acid, 1-methylethyl ester) is one of fibrate drugs. There have been a lot of efforts to improve a fenofibrate formulation, particularly bioavailability of fennofibrate. U.S. Pat. Nos. 4,895,726 and 5,880,148 disclose that fenofibrate is co-micronized with a surfactant.

Several patents disclose specific formulations of micronized fenofibrate and a specific polymer additive or surfactant additive, while other patents disclose fenofibrate emulsion and suspension.

US Patent No. 20030224059 discloses a micronized particle formed of an active pharmaceutical ingredient having low water solubility and a solid solution of a sublimable carrier, a drug delivery vehicle comprising the same, and a preparation method thereof.

Micronization of fenofibrate or combination of a surfactant and micronized fenofibrate may increase bioavailability of fenofibrate to some degree, thus decreasing administration amount thereof while maintaining the bioavailability at eating. However, since practical bioavailability of fenofibrate is still low and the use of a surfactant may induce toxicity to human body, there is still a demand for the improvement.

SUMMARY OF THE INVENTION

The present invention provides a technology capable of remarkably increasing water solubility in order to increase bioavailability of a poorly soluble drug.

One aspect of the present invention provides a poorly soluble drug containing microsphere in the form of a solid dispersion wherein the poorly soluble drug is dispersed in an aqueous polymer carrier in a noncrystalline form by spray drying.

Another aspect provides an oral formulation comprising the poorly soluble drug containing microsphere.

Yet another aspect provides a method of manufacturing a poorly soluble drug containing microsphere comprising a) dissolving a water-soluble polymer carrier and a poorly soluble drug in water and an organic solvent to prepare a mixed solution; and b) spray drying the mixed solution.

DESCRIPTION OF THE EMBODIMENT

Figure 1:
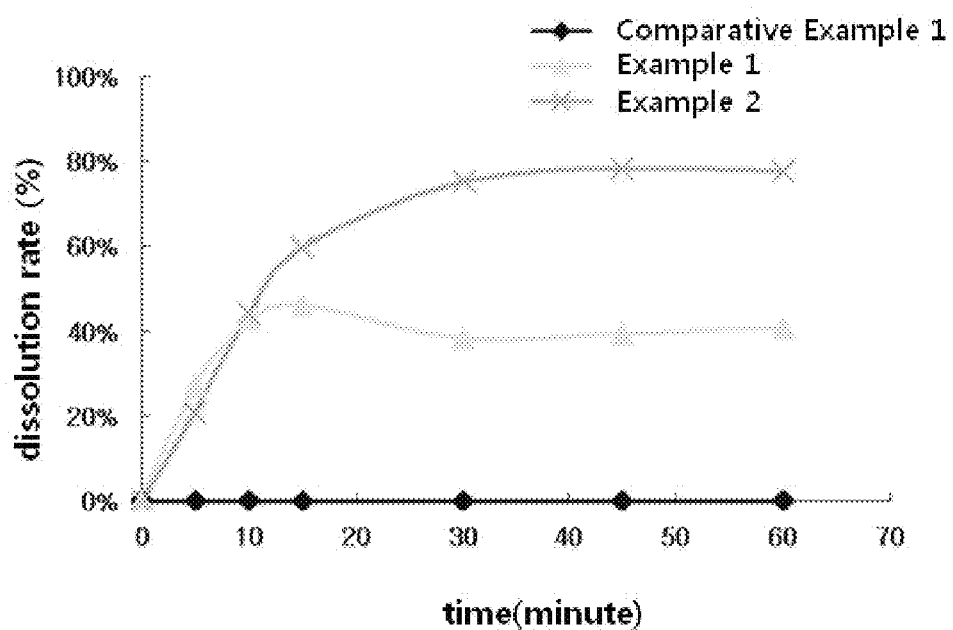
FIG. 1 is a dissolution result graph of Experimental Example 1.

The present invention provides a poorly soluble drug containing microsphere in the form of a solid dispersion wherein a poorly soluble drug is dispersed in a water-soluble polymer carrier in a noncrystalline form by spray drying.

The present invention also provides a method manufacturing the poorly soluble drug containing microsphere comprising dissolving a water-soluble polymer carrier and a poorly soluble drug in water and an organic solvent to prepare a mixed solution; and spray drying the mixed solution.

The present invention uses water and an organic solvent together to completely dissolve a poorly soluble drug and an a water-soluble polymer, and obtains a microsphere by spray drying the completely dissolved solution. Specifically, in the poorly soluble drug containing microsphere of the present invention, the poorly soluble drug is dispersed in a noncrystalline form in a water-soluble polymer carrier, by spray drying a mixed solution wherein the water-soluble polymer carrier and the poorly soluble drug are dissolved in water and an organic solvent.

One aspect of the invention relates to a poorly soluble drug containing microsphere in the form of a solid dispersion wherein the poorly soluble drug is dispersed in a water-soluble polymer carrier in a noncrystalline form, which is obtained by spray drying a mixed solution comprising the poorly soluble drug, the water-soluble polymer carrier, water and an organic solvent.

The mixed solution may be a mixed solution of an aqueous solution of the water-soluble polymer carrier dissolved in water and a solution of the poorly soluble drug dissolved in the organic solvent; or a mixed solution wherein the poorly soluble drug is dissolved in a solution of the water-soluble polymer carrier dissolved in a mixed solvent of the organic solvent and water.

The poorly soluble drug may have water solubility of less than 1-10 mg/ml. One example may include a drug corresponding to BCS (Biopharmaceutics Classification System) class IV, and the specific examples may include acyclovir, allopurinol, amiodarone, azathioprine, benazepril, calcitriol, candesartan, eprosartan, carbidopa/levidopa, clarithromycin, clozapine, desmopressin acetate, diclofenac, enalapril, famotidine, felodipine, fenofibrate, fentanyl, fexofenadine, fosinopril, furosemide, glyburide, hyoscyamine, imipramine, itraconazole, levothyroxine, atorvastatin, lovastatin, meclizine, megesterol, mercaptopurine, metolazone, mometasone, nabumetasone, omeprazole, paroxetine, propafenone, quinapril, simvastatin, sirolimus, tacrolimus, tizanidine, and a combination thereof, but not limited thereto. More specifically, it may include atorvastatin, simvastatin, candesartan, eprosartan, fenofibrate, sirolimus, tacrolimus, and the like.

The water-soluble polymer carrier may include any carriers as long as it may be commonly used for improving solubility of a poorly soluble drug. According to one embodiment of the invention, it may include pharmaceutically acceptable water-soluble polymer, specifically one or more selected from the group consisting of hydroxypropylmethylcellulose (HPMC, for example, those having weight average molecular weight of about 10,000 to 1,500,000), polyethyleneglycol (PEG, for example, those having weight average molecular weight of 3,000 to 9,000), polyvinylpyrrolidone (PVP, for example, those having weight average molecular weight of 2,500 to 2,500,000), cellulose, and a combination thereof, more specifically, HPMC.

The poorly soluble drug is dispersed in the water-soluble polymer carrier in a noncrystalline form.

Preferably, the hydroxypropylmethylcellulose (HPMC) may be those wherein about 16.5 to 30% specifically about 28 to 30% of hydroxyl groups are methoxylated, and about 4 to 32%, specifically about 7 to 12% of hydroxy groups are substituted by hydroxyl propyl groups. The HPMC may have an average molecular weight of 10,000 to 1,500,000 g/mol.

According to one embodiment of the invention, the weight ratio of the poorly soluble drug and the water-soluble polymer carrier in the microsphere may be 1:1 to 1:15, preferably 1:1 to 1:10, most preferably 1:1 to 1:5. If the water-soluble polymer carrier is less than 1:1, drug may not be sufficiently dispersed and thus solubility may not be improved. And, if it exceeds 1:15, viscosity may be increased due to the water-soluble carrier thus causing a problem in performing spray drying, while solubility may not be increased no longer.

According to one embodiment, the microsphere may further include at least one selected from the group consisting of a disintegrating agent, a stabilizer, and pharmaceutically acceptable lubricant, an opacifier, a colorant, pharmaceutically acceptable excipient, and the like, specifically talc. The content of the excipient may be 0.01 to 10 wt %, preferably 1 to 5 wt %, based on total weight of a mixed solution comprising a poorly soluble drug, a water-soluble polymer carrier, water and an organic solvent. If the content is lower than the above range, satisfactory excipient function may not be obtained, and if it exceeds the above range, it may deteriorate microsphere properties.

The microsphere containing the poorly soluble drug dispersed in a noncrystalline form of the present invention may have an uniform sphere size, and have a particle size (average particle diameter) of 500 μm or less, specifically 350 μm or less, more specifically 100 μm or less. By dissolving the poorly soluble drug in a solvent, the drug may be noncrystallized, and dispersed in the carrier in this state, and thus, solubility and absorption may be improved. For example, the average particle diameter of the microsphere may be 1 μm to 500 μm, specifically, 10 μm to 350 μm, more specifically 10 μm to 100 μm.

The present invention provides a method of manufacturing a microsphere comprising a) dissolving a poorly soluble drug and a water-soluble polymer carrier in an organic solvent and water to prepare a mixed solution; and b) spray drying the mixed solution.

According to the present invention, a relatively spherical microsphere may be smoothly formed by spray drying of a mixed solution where the poorly soluble drug and a water-soluble polymer are dissolved, without using a seed for forming particles. And, by simultaneously using an organic solvent and water, a poorly soluble drug may be uniformly dispersed in a water-soluble polymer carrier without using a surfactant which is commonly used for improving solubility and may induce toxicity to human body.

In the manufacture of the microsphere, to obtain spherical uniform particles, a particle is commonly prepared by coating on a seed. However, if a seed or particle is included in a solution, it may be difficult to spray dry while uniformly dispersing, and thus, uniformity of mixing may not be secured. Further, if a fluidized bed coating method is applied using mixing uniformity, a lot of time and cost may be required. Therefore, to form relatively spherical uniform particles without a seed, it may be necessary to appropriately control process conditions when spray drying.

The kind and content of the poorly soluble drug and the water-soluble polymer carrier used in the manufacturing step are as explained above.

The organic solvent may be selected from the group consisting of $C_1$-$C_4$ linear or branched alcohol (for example, ethanol, methanol, and the like), dichloromethane, and a combination thereof, preferably ethanol. The organic solvent and water may be mixed after the organic solvent is used for dissolving a poorly soluble drug and the water is used for dissolving the water-soluble polymer carrier, or they may be used for dissolving the water-soluble polymer carrier and the poorly soluble drug in the form of a mixed solvent (co-solvent) of water and organic solvent. According to one embodiment of the invention, the weight ratio of the organic solvent and water may be 0.5:1 to 5:1, preferably 1:1 to 3:1 (weight of organic solvent: weight of water). If the content of the organic solvent is greater than the above range, the water-soluble polymer carrier may be not dissolved. And if the content of the water is greater than the above range, drug may be precipitated. And, if the carrier is not completely dissolved in the solvent, spraying may become difficult due to high viscosity, and uniform particles may not be obtained. However, if water and the organic solvent are simultaneously used in the present invention, the water-soluble polymer carrier and the poorly soluble drug may be completely dissolved in a solvent and thus facilitating spray drying.

In the mixed solution comprising the poorly soluble drug, the water-soluble polymer carrier, the organic solvent and water, the concentration of the poorly soluble drug and the water-soluble polymer carrier may be 1 to 20 wt %, specifically 3 to 15 wt %, more specifically 5 to 10 wt %. If the concentration of the drug and the polymer is less than 1 wt %, spray drying time may become long, and if it exceeds 20 wt %, spray drying may not be conducted due to high viscosity.

According to one embodiment, the step a) may comprise dissolving the water-soluble polymer carrier in water to prepare an aqueous solution of the polymer carrier, dissolving the poorly soluble drug in an organic solvent to prepare a solution of the poorly soluble drug, and mixing the aqueous solution of the polymer carrier and the solution of the poorly soluble drug to prepare the mixed solution. Alternatively, it may comprise dissolving the water-soluble polymer carrier in a co-solvent of water and an organic solvent to prepare a solution of the polymer carrier, and dissolving the poorly soluble drug in the polymer carrier solution to prepare a mixed solution.

In the step b), the mixed solution of the step a) is spray dried, and the spray method may be conducted using a nozzle type spray drier or an atomizer type spray drier, and the like.

In a nozzle type spray drying, to form particles of uniform and appropriate size, injection temperature may be 80 to 120° C., specifically 90 to 110° C., and injection speed may be 1 to 10 ml/min, specifically 3 to 5 ml/min.

In an atomizer type spray drying, to form particles of uniform and appropriate size, spray temperature may be controlled to 80 to 120° C., specifically 90 to 110° C. And, spray speed may be 3,000 to 5,000 rpm, specifically 3,500 to 4,500 rpm, and injection speed of the mixed solution may be 10 to 100 ml/min, specifically 40 to 70 ml/min. If the atomizer type spray drier is used, uniform particles may be prepared and thus it may be advantageous for improving dissolution.

According to one embodiment of the invention, excipient comprising talc may be added to the mixed solution, before the step a) spraying of the mixed solution. The content of the excipient may be 0.01 to 10 wt %, preferably 1 to 5 wt % based on total weight of the mixed solution. If the content of the excipient is less than the above range, satisfactory excipient function may not be obtained, and if it exceeds the above range, microsphere properties may be deteriorated.

Meanwhile, another aspect of the invention is related to an oral formulation comprising the microsphere.

According to one embodiment of the invention, the microsphere may be prepared as an oral formulation. And, pharmaceutically acceptable excipient, disintegrating agent, a binder, a stabilizer, a colorant, a sweetener, lubricant, and the like may be added to the prepared microsphere, to prepare powder, a granule, a capsule, a tablet, and the like. A preferable dosage form is a tablet. If the microsphere is prepared in the form of a tablet, a coating agent and/or a plasticizer may be contained according to a common method to formulate the tablet in the form of a fast dissolving oral tablet or a coating tablet.

The dosage of the poorly soluble drug may be varied according to the kinds of drug, the kind and severity of disease, age of a patient, and the like.

The poorly soluble drug containing microsphere of the present invention is a microsphere in the form of a solid dispersion wherein the poorly soluble drug is dispersed in a water-soluble polymer carrier in a noncrystalline form. It may remarkably improve solubility compared to a dosage form for improving solubility using a micronized poorly soluble drug. And, according to the present invention, a spherical spray dried microsphere may be prepared without a seed, and a surfactant that may induce toxicity to human body is not used for improving solubility.

According to one embodiment of the invention, provided is a composition comprising a poorly soluble drug containing microsphere wherein fenofibrate is dispersed in a water-soluble polymer carrier in a noncrystalline form, which is prepared by spray drying, simultaneously using an organic solvent and water. Specifically, the microsphere may comprise the fenofibrate and the water-soluble polymer carrier in the weight ratio of 1:1 to 1:15, preferably 1:1 to 1:10, most preferably 1:1 to 1:5, thereby showing the following dissolution pattern. Specifically, it may exhibit a dissolution pattern that 10 wt % or more, preferably 20 wt % or more of contained fenofibrate is dissoluted within 5 minutes, 30 wt % or more, preferably 50 wt % or more is dissoluted within 15 minutes, and 40 wt % or more, preferably 70 wt % or more is dissoluted within 30 minutes, when tested according to the second method (paddle method: 100 rotations per minute, tertiary distilled water 500 ml) of Korean Pharmacopoeia $9^{th}$ Revision.

The poorly soluble drug containing microsphere of the present invention may improve water solubility of poorly soluble drug, and thereby, improve bioavailability of the poorly soluble drug.

EXAMPLES

Hereinafter, the present invention will be explained in detail with reference to the following Examples.

Although the present invention is described in connection with practical exemplary embodiments, it is to be understood that various modifications and changes can be made within the spirit and scope of the appended claims.

In addition to the above explained embodiments, various embodiments are included within the appended claims.

Example 1

10 g of HPMC (2910 series, ShinEtsu Chemical, hereinafter, the same) was mixed with 90 g of water and agitated to prepare a completely dissolved 10% w/w solution. 2 g of fenofibrate was mixed with 200 g of ethanol and agitated to completely dissolve. The two solutions were mixed and agitated again to prepare a solution without precipitations. The weight ratio of fenofibrate and HPMC was 1:5 (weight of fenofibrate: weight of HPMC).

The solution was spray dried with a nozzle type spray drier (Mini spray dryer B-290, Buchi) at a injection temperature of 90° C. and injection amount of 3 mL/min, to obtain a fenofibrate containing microsphere of a relative spherical shape with an average particle size of 50 μm.

Example 2

450 g of HPMC and 2550 g of water were mixed and agitated to prepare a completely dissolved 15% w/w solution. 90 g of fenofibrate and 5500 g of ethanol were mixed and agitated to completely dissolve. The two solutions were mixed and agitated again to prepare a solution without precipitations. The weight ratio of fenofibrate and HPMC was 1:5.

The solution was spray dried with an atomizer type spray drier (DJE-003R, Donjin Spray Drying Technology), at a spray temperature of 110° C., injection amount of 45 mL/min, and atomizer speed of 3,500 rpm, to obtain a fenofibrate containing microsphere of a relatively spherical shape with a size of 50 μm.

Comparative Example 1

Crystalline fenofibrate was used as it is instead of being made into a microsphere.

Comparative Example 2

A fenofibrate containing microsphere was to be prepared with an atomizer type spray drier using only ethanol or only water as a solvent, using the same amounts of fenofibrate, HPMC and a solvent as Example 2. However, HPMC and fenofibrate could not be dissolved in only ethanol or in only water, and thus, a microsphere could not be prepared.

Experimental Example 1

For the microspheres obtained in Example 1, Example 2 and Comparative Example 1, dissolution test was performed under the following conditions, and the results are shown in FIG. 1.

Dissolution test conditions are as follows.
Test method: the second method of Korean Pharmacopoeia $9^{th}$ Revision (Paddle method)
Apparatus: LABFINE Dissolution tester (Model name DST-810, Wrap Fine Co. Ltd)
dissolution solution: 500 mL water
temperature: 37±0.5° C.
paddle rotation speed: 100 rpm The poorly soluble drug containing microspheres with uniform distribution (Examples 1 and 2) exhibited excellent dissolution compared to the crystalline poorly soluble drug (Comparative Example 1), in vitro dissolution test.

Example 3

The following ingredients were mixed with the compositional ratio as described in the Table 1 by the same method as Example 2 to prepare a yellowish clear mixed solution, which was allowed to stand so that bubbles may disappear.

TABLE 1

|  | Weight ratio | Amount (g) |
|---|---|---|
| HPMC | 3 | 300 |
| Water |  | 1,700 |
| Ethanol |  | 4,000 |
| Fenofibrate | 1 | 100 |
|  |  | 6,100 |

The solution was spray dried with an atomizer type spray drier at a spray temperature of 110° C., injection amount of 45 mL/min, and atomizer speed of 3,500 rpm, to obtain a fenofibrate containing microsphere of a relatively spherical shape with a size of 50 μm.

Example 4

The following ingredients were mixed with the compositional ratio as described in the Table 2 by the same method as Example 2 to prepare a yellowish clear mixed solution, which was allowed to stand so that bubbles may disappear.

TABLE 2

|  | Weight ratio | Amount (g) |
|---|---|---|
| HPMC | 4 | 300 |
| Water |  | 1,700 |
| Ethanol |  | 4,000 |
| Fenofibrate | 1 | 75 |
|  |  | 6,075 |

The solution was spray dried with an atomizer type spray drier at a spray temperature of 110° C., injection amount of 36 mL/min, and atomizer speed of 3,500 rpm, to obtain a fenofibrate containing microsphere of a relatively spherical shape with a size of 50 μm.

Example 5

The following ingredients were mixed with the compositional ratio as described in the Table 3 by the same method as Example 2 to prepare a yellowish clear mixed solution, which was allowed to stand so that bubbles may disappear.

TABLE 3

|  | Weight ratio | Amount (g) |
|---|---|---|
| HPMC | 5 | 300 |
| Water |  | 1,700 |
| Ethanol |  | 4,000 |
| Fenofibrate | 1 | 60 |
|  |  | 6,060 |

Figure 2:
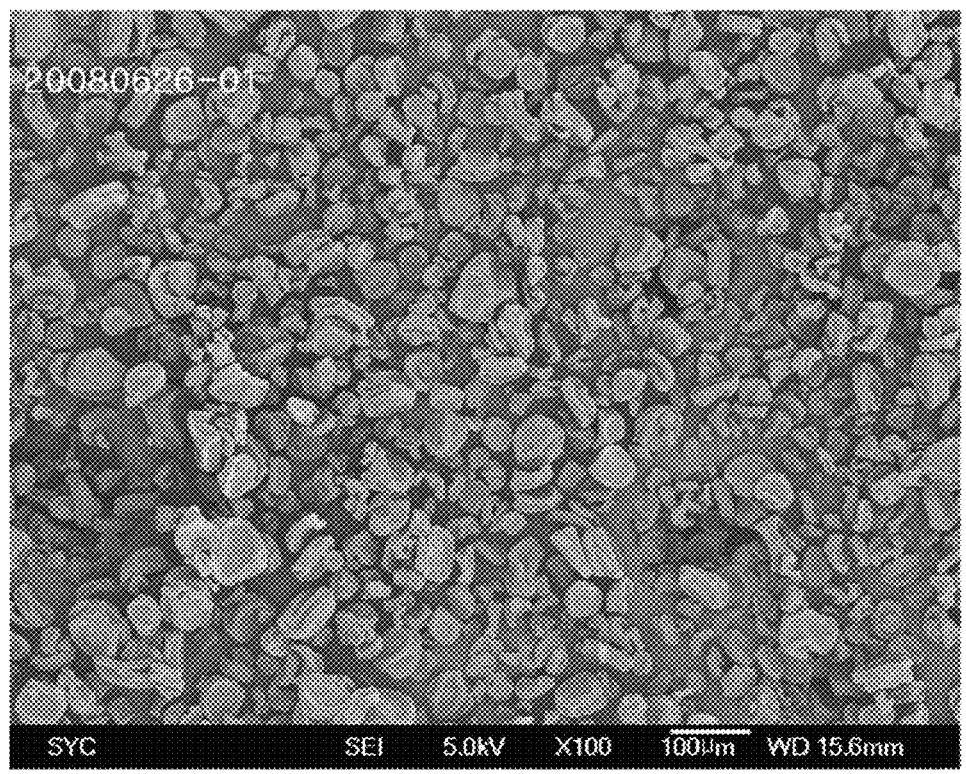
FIG. 2 is an SEM photograph of the microsphere of Example 5.

The solution was spray dried with an atomizer type spray drier at a spray temperature of 100° C., injection amount of 45 mL/min, and atomizer speed of 3,500 rpm. It is confirmed by SEM that the microsphere prepared in Example 5 has a particle size of 50 μm or less (FIG. 2)

Example 6

With the compositional ratio as described in the following Table 4, HPMC was put in a mixed solvent of water and ethanol and properly mixed, and then, fenofibrate was introduced therein and agitated to completely dissolve, thus preparing a yellowish clear mixed solution, which was allowed to stand so that bubbles may disappear.

TABLE 4

|  | Amount (g) |
| --- | --- |
| HPMC | 300 |
| Water | 1,425 |
| Ethanol | 4,275 |
| Fenofibrate | 60 |
|  | 6,060 |

The solution was spray dried with an atomizer type spray drier at a spray temperature of 100° C., injection amount of 45 mL/min, and atomizer speed of 3,500 rpm. It was confirmed that the microsphere prepared in Example 6 has a particle size of 50 μm or less.

Experimental Example 2

Figure 3:
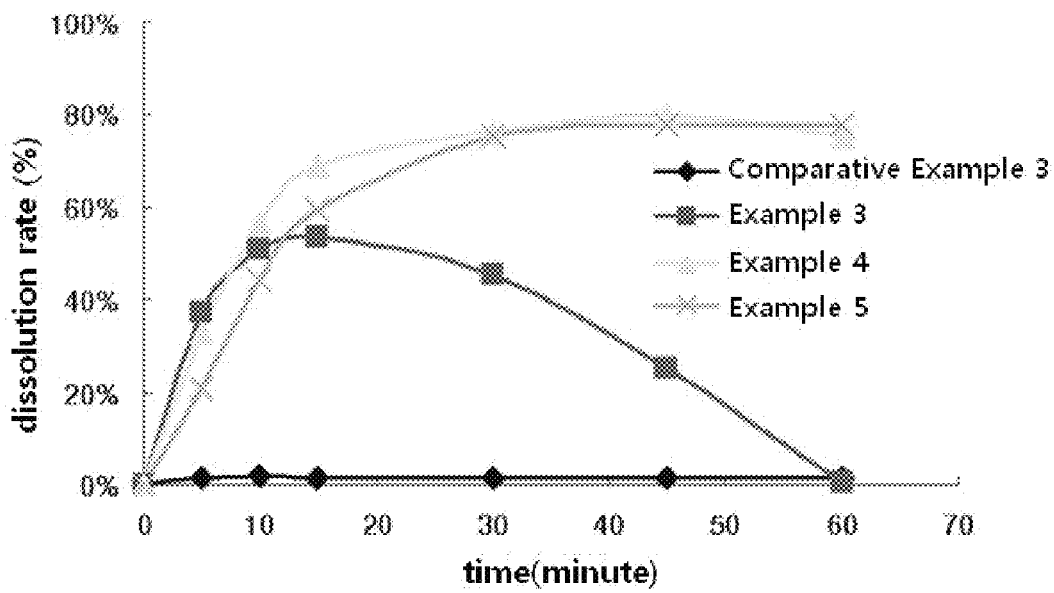
FIG. 3 is a dissolution result graph of Experimental Example 2.

For the microspheres of Examples 3 to 5, and "Lipidil Supra®" (Comparative Example 3, Greencross) which is a formulation of which solubility is improved using micronized poorly soluble drug, in vitro dissolution test was performed by the same method as Experimental Example 1, and the results were shown in FIG. 3.

The particles of Examples 3 to 5 exhibited very excellent initial dissolution rate. Particularly, the poorly soluble drug microspheres of Example 4 and Example 5 exhibited 80% or more dissolution without rapid decrease in solubility until 1 hour, and the difference in dissolution rate between the two groups was not significant. To the contrary, in the case of a commercial formulation of Comparative Example 3, dissolution rate was nearly 0 even until 1 hour has elapsed, and thus, it can be seen that dissolution hardly occurs.

Example 7 and Experimental Example 3

The following ingredients were mixed with the compositional ratio as described in the following Table 5 by the same method as Example 2 to prepare a yellowish clear mixed solution, which was allowed to stand so that bubbles may disappear.

TABLE 5

|  | Weight ratio | Amount (g) |
| --- | --- | --- |
| HPMC | 5 | 300 |
| Water |  | 1,700 |
| Ethanol |  | 4,000 |
| Simvastatin | 1 | 60 |
|  |  | 6,060 |

The solution was spray dried with an atomizer type spray drier at a spray temperature of 100° C., injection amount of 45 mL/min, and atomizer speed of 3,500 rpm, to obtain a simvastatin microsphere in the form of a solid dispersion of a relatively spherical shape with a size of 50 μm.

Figure 4:
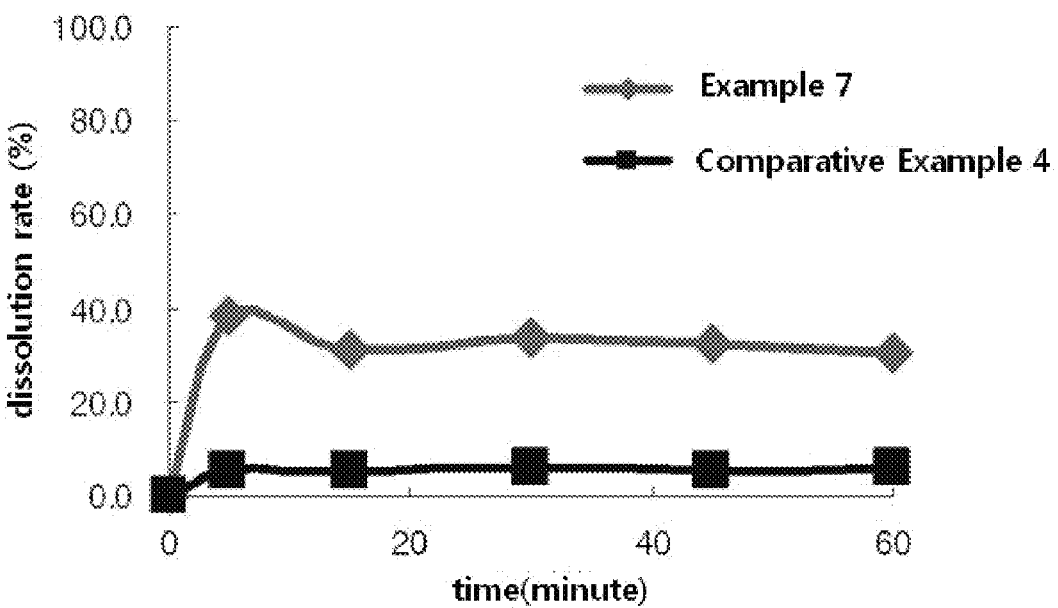
FIG. 4 is a dissolution result graph of Experimental Example 3.

For the microsphere, in vitro dissolution test was performed by the same method as Experimental Example 1, and the result was shown in FIG. 4. For comparison, the existing commercialized formulation Zocor® (Comparative Example 4, MSD) was used. From FIG. 4, it can be seen that the microsphere of the present invention has excellent dissolution rate.

Example 8 and Experimental Example 4

The following ingredients were mixed with the compositional ratio as described in the following Table 6 by the same method as Example 2 to prepare a yellowish clear mixed solution, which was allowed to stand so that bubbles may disappear.

TABLE 6

|  | Weight ratio | Amount (g) |
| --- | --- | --- |
| HPMC | 5 | 300 |
| Water |  | 1,700 |
| Ethanol |  | 4,000 |
| Candesartan | 1 | 60 |
|  |  | 6,060 |

The solution was spray dried with an atomizer type spray drier at a spray temperature of 100° C., injection amount of 45 mL/min, and atomizer speed of 3,500 rpm, to prepare a candesartan microsphere in the form of a solid dispersion of a relatively spherical shape. It was confirmed that the prepared microsphere has a particle size of 50 μm. For the obtained miscrosphere, in vitro dissolution test was performed by the same method as Experimental Example 1 and the result was shown in FIG. 5. As control, the existing commercialized formulation "Atacand®" (Comparative Example 15, AstraZeneca Korea) was used.

Figure 5:
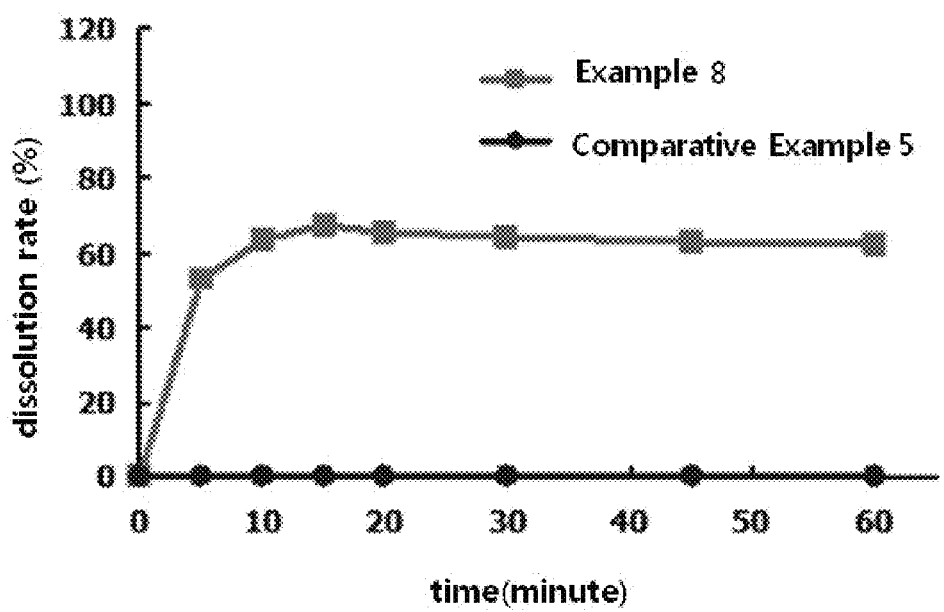
FIG. 5 is a dissolution result graph of Experimental Example 4.

As shown in FIG. 5, the microsphere of the present invention has remarkably excellent dissolution rate compared to Comparative Example 5.

Example 9 and Experimental Example 5

The following ingredients were mixed with the compositional ratio as described in the following Table 7 by the same method as Example 2 to prepare a yellowish clear mixed solution, which was allowed to stand so that bubbles may disappear.

TABLE 7

|  | Weight ratio | Amount (g) |
| --- | --- | --- |
| PVP(MW 7,000~11,000, BASF) | 5 | 300 |
| Water |  | 1,700 |
| Ethanol |  | 4,000 |
| Candesartan | 1 | 60 |
|  |  | 6,060 |

* MW: weight average molecular weight

Figure 6:
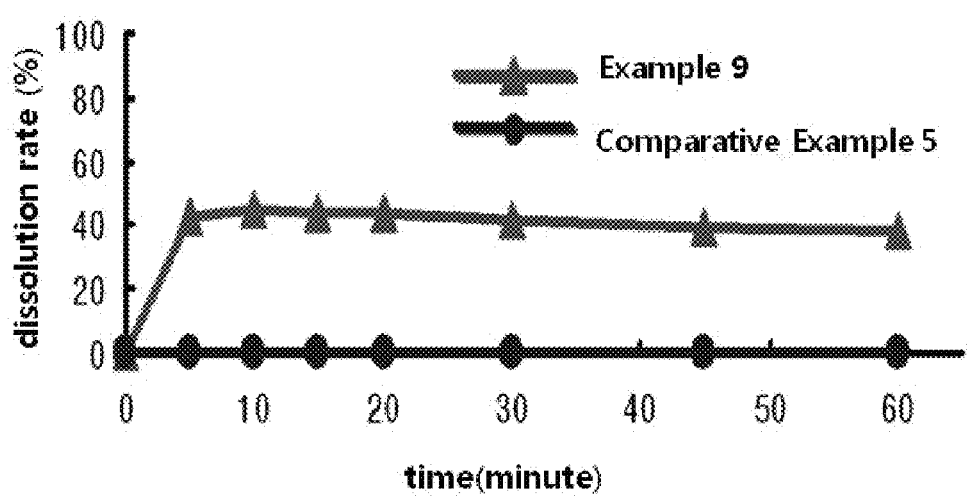
FIG. 6 is a dissolution result graph of Experimental Example 5.

The solution was tested by the same method as Example 8 and Experimental Example 4, and the result was shown in FIG. 6. As control, the existing commercialized formulation "Atacand®" (Comparative Example 5) was used. As shown in FIG. 6, the microsphere of the present invention has excellent dissolution rate compared to Comparative Example 5.

Example 10 and Experimental Example 6

The following ingredients were mixed with the compositional ratio as described in the following Table 8 by the same method as Example 2 to prepare a yellowish clear mixed solution, which was allowed to stand so that bubbles may disappear.

TABLE 8

|  | Weight ratio | Amount (g) |
| --- | --- | --- |
| HPMC | 5 | 300 |
| Water |  | 1,700 |
| Ethanol |  | 4,000 |
| Tacrolimus | 1 | 60 |
|  |  | 6,060 |

As the HPMC, the same one as used for fenofibrate was used.

Figure 7:
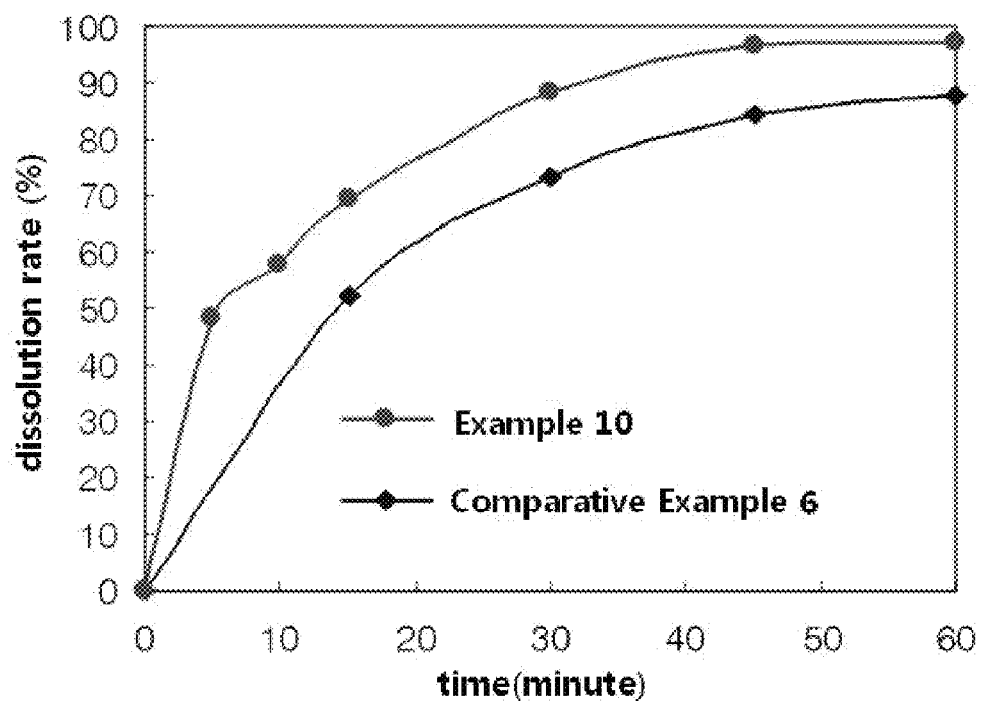
FIG. 7 is a dissolution result graph of Experimental Example 6.

The solution was spray dried with an atomizer type spray drier at a spray temperature of 100° C., injection amount of 45 mL/min, and atomizer speed of 3,500 rpm, to prepare a tacrolimus microsphere in the form of a solid dispersion of a relatively spherical shape. It can be seen that the prepared microsphere has a particle size of 50 μm or less. For the obtained microsphere, in vitro dissolution test was performed by the same method as Experimental Example 1, and the result was shown in FIG. 7. For comparison, the existing solubility improving agent "Prograf®" (Comparative Example 6, Astellas) was used. As shown in FIG. 7, the microsphere of the present invention has excellent dissolution rate compared to Comparative Example 6.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

The invention claimed is:

1. A method for preparing a poorly soluble drug containing microsphere, comprising
a) dissolving a water-soluble polymer carrier and a poorly soluble drug in water and an organic solvent to prepare a mixed solution; and b) spray drying the mixed solution,
wherein the mixed solution does not include a surfactant, the weight ratio of the organic solvent and water is 0.5:1 to 5:1, and the poorly soluble drug is fenofibrate, and
wherein the spray drying is conducted at a spray temperature of 80 to 120° C., a spray speed of 3,000 to 5,000 rpm, and an injection speed of 10 to 100 ml/min, using an atomizer type spray dryer, and
wherein the weight ratio of the organic solvent and water is 1:1 to 3:1
wherein the water-soluble polymer carrier is hydroxypropylmethylcellulose (HPMC), and the organic solvent is ethanol.

2. The method according to claim 1, wherein a seed is not used.

3. The method according to claim 1, wherein the weight ratio of the fenofibrate and the HPMC is 1:1 to 1:15.

4. The method according to claim 1, wherein the b) spray drying is conducted at a spray temperature of 90 to 110° C., a spray speed of 3,500 to 4,500 rpm, and an injection speed of 40 to 70 ml/min, using an atomizer type spray dryer.

5. The method according to claim 1, wherein the step a) comprises
dissolving the HPMC in water to prepare an aqueous solution of the HPMC polymer carrier, dissolving the fenofibrate in the ethanol to prepare a solution of the fenofibrate, and mixing the aqueous solution of the HPMC and the solution of the fenofibrate to prepare a mixed solution; or
dissolving the HPMC in a mixed solvent of water and the ethanol to prepare a solution of the HPMC, and dissolving the fenofibrate in the HPMC solution to prepare a mixed solution.

6. The method according to claim 1, wherein the wherein the fenofibrate is dispersed in the HPMC in a non-crystalline form.

* * * * *